(12) United States Patent
Elgas et al.

(10) Patent No.: US 6,638,479 B1
(45) Date of Patent: Oct. 28, 2003

(54) VARIABLE PACKING DENSITY IN HOLLOW FIBER DEVICE

(75) Inventors: Roger J. Elgas, Anaheim Hills, CA (US); Robert F. Gremel, Huntington Beach, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/416,146

(22) Filed: Oct. 11, 1999

(51) Int. Cl.⁷ .......................... A61M 1/14; A61M 37/00
(52) U.S. Cl. ......................................... 422/45; 604/4.01
(58) Field of Search ................... 422/44–48; 604/4.01, 604/6.14

(56) References Cited

U.S. PATENT DOCUMENTS

| | | | |
|---|---|---|---|
| 3,422,008 A | 1/1969 | McLain | 210/22 |
| 3,602,446 A | 8/1971 | Kawashima et al. | 242/18 |
| 4,033,107 A | 7/1977 | Sasayama et al. | 57/81 |
| 4,237,013 A | * 12/1980 | Yamazaki et al. | 210/321.8 |
| 4,268,279 A | 5/1981 | Shindo et al. | 55/16 |
| 4,533,089 A | 8/1985 | Sartor et al. | 242/7.21 |
| 4,622,206 A | 11/1986 | Torgeson | 422/48 |
| 4,923,679 A | 5/1990 | Fukasawa et al. | 422/48 |
| 5,043,140 A | 8/1991 | Combs | 422/46 |
| RE33,932 E | 5/1992 | Fukasawa et al. | 422/46 |
| 5,137,531 A | 8/1992 | Lee et al. | 422/46 |
| 5,162,101 A | 11/1992 | Cosentino et al. | 422/46 |
| 5,270,004 A | 12/1993 | Cosentino et al. | 422/46 |
| 5,299,749 A | * 4/1994 | Thorogood et al. | 242/437.3 |
| 5,346,621 A | * 9/1994 | Haworth et al. | 210/645 |
| 5,354,470 A | 10/1994 | Seita et al. | 210/500 |
| 5,429,184 A | 7/1995 | Bach et al. | 165/149 |
| 5,489,413 A | 2/1996 | Carson et al. | 422/46 |
| 5,706,889 A | 1/1998 | Bach et al. | 165/172 |
| 5,718,869 A | 2/1998 | Bach et al. | 422/45 |
| 5,762,869 A | * 6/1998 | White et al. | 422/45 |
| 5,837,033 A | * 11/1998 | Giglia et al. | 95/45 |
| RE36,125 E | 3/1999 | Haworth et al. | 422/46 |
| 6,117,390 A | * 9/2000 | Corey, Jr. | 422/44 |

* cited by examiner

*Primary Examiner*—Angela D. Sykes
*Assistant Examiner*—Leslie R. Deak
(74) *Attorney, Agent, or Firm*—Thomas G. Berry; Daniel W. Latham

(57) ABSTRACT

The efficiency of a hollow fiber wound oxygenator is improved by varying the packing density of the fiber bundle in a direction longitudinal and/or circumferential of the core.

4 Claims, 2 Drawing Sheets

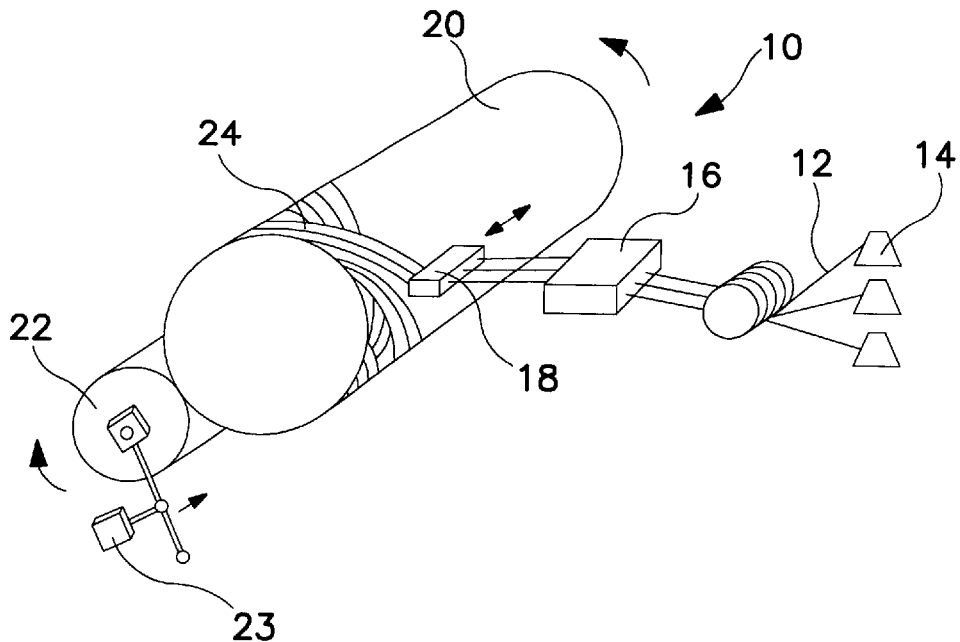
FIG. 1
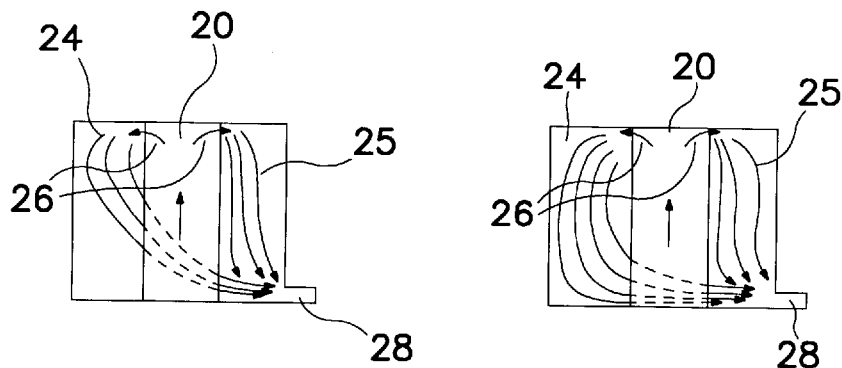
FIG. 2a
PRIOR ART
FIG. 2b
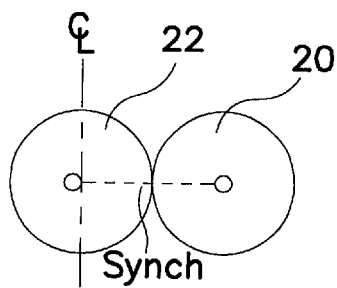
FIG. 3
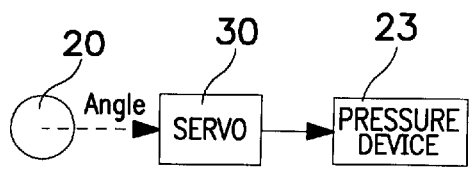
FIG. 4a

VARIABLE PACKING DENSITY IN HOLLOW FIBER DEVICE

FIELD OF THE INVENTION

This invention relates to methods and apparatus for obtaining a variable packing density of hollow fibers in wound fiber cartridges such as oxygenators, and more particularly to the variation of packing density throughout the thickness of the cartridge.

BACKGROUND OF THE INVENTION

Blood oxygenator cartridges are typically made by winding hollow fibers onto a core in a criss-cross pattern until the successive layers of fibers build up into a bundle of desired thickness. The core 1.5 and fiber bundle are then inserted into a cylindrical cartridge housing. The ends of the fiber bundle are potted in the housing and are then cut so as to form a multitude of individual fibers extending longitudinally through the cartridge. Oxygen is introduced into the fibers at one of their potted ends, and blood is introduced into the cartridge to flow over and around the oxygenated fibers. The fibers act as a membrane through which oxygen migrates to bond with blood cells as they contact the fibers, and to drive carbon dioxide back into the fibers.

The hollow membrane fibers used in oxygenators are very expensive and account for about 30% of the cost of the oxygenator. At an outside diameter of about 300 microns, they are also very delicate and must be wound with an essentially constant tension.

It is thus desirable to use a minimum amount of fiber in an oxygenator cartridge, but such minimization is limited by the fact that enough fiber surface must be provided to allow most or all blood cells to contact a fiber during their transit through the oxygenator. The efficiency of the oxygenator can be greatly improved by minimizing any laminar blood flow patterns through the fiber bundle, so as to cause the blood stream to mix thoroughly as it traverses the cartridge. Also, the geometry of a typical oxygenator is such that blood enters the fiber bundle more or less evenly around the circumference of the fiber bundle but exits it at a single point on its circumference. Consequently, the blood flow is not even throughout the fiber bundle.

In order to reduce the radial extent of the fiber bundle, it is customary to pack the fibers during winding by pressing a packing roller against the outside of the fiber bundle as it is being wound. The pressure of the packing roller causes the fibers of each layer to lie firmly against the fibers of the preceding layer. The amount of packing pressure determines at least in part the blood flow characteristics of the fiber bundle. Too little pressure allows the formation of laminar flow channels; too much impedes the flow of blood.

It has previously been proposed in U.S. Pat. No. Re. 36,125 to Haworth et al. that the efficiency of an oxygenator could be improved by increasing the packing fraction (i.e. the fraction of a unit volume of bundle space occupied by fiber) in successive radially outward sections of the fiber bundle. This process, however, still admits of a uniformity within each section that promotes the formation of laminar flow channels, and it does not help the uneven distribution of blood flow around the circumference of the fiber bundle.

SUMMARY OF THE INVENTION

The present invention promotes mixing of the blood in a fiber-wound oxygenator by discouraging the formation of laminar flow patterns. It also causes the blood flow to be distributed more evenly around the circumference of the fiber bundle. The invention achieves this result by varying the packing density of the fibers longitudinally and/or circumferentially of the bundle. This is preferably achieved by cyclically varying the shuttle speed or packing pressure, and/or by using packing rollers with an irregular geometry.

BRIEF DESCRIPTION OF THE DRAWINGS

FIG. 1 is a schematic perspective view of the winding mechanism used in the invention;

FIG. 2a is a schematic blood flow diagram through a prior art oxygenator;

FIG. 2b is a schematic blood flow diagram through an oxygenator using the invention;

FIG. 3 is a schematic diagram illustrating a first embodiument of the invention;

FIG. 4a is a block diagram illustrating a second embodiment of the invention;

FIG. 4b is a core-angle pressure diagram illustrating the operation of the embodiment of FIG. 4a;

DESCRIPTION OF THE PREFERRED EMBODIMENT

Figure 4B:
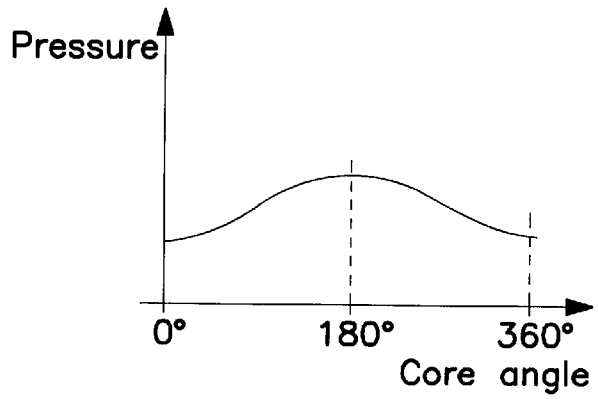

FIG. 1 schematically shows a conventional winding apparatus 10 for fiber-wound oxygenators. Fibers 12 are wound from bobbins 14 through a tensioning device 16 and a shuttle 18 onto a rotating core 20. The shuttle 18 reciprocates longitudinally of the core 20, and thus winds the fibers 12 onto the core 20 in a criss-cross pattern.

A packing roller 22 is pressed against the wound fibers 12 by a mechanism sumbolically shown as 23 so as to pack successive layers of fibers 12 against each oher. The packing roller 22 is conventionally so mounted as to exert a constant uniform pressure against the bundle 24 of fibers 12 as the diameter of bundle 24 grows during the winding operation.

Oxygenators made in the above-described conventional manner have two properties that reduce their efficiency. The first is illustrated in FIG. 2a. With the core 20 in a vertical position, blood (arrows 25) is introduced into the fiber bundle 24 through the core 20 at many points 26 around the top of the core 20. At the bottom of the core 20, however, all of the blood is channeled into a single outlet fitting 28. As indicated by the arrows 25 in FIG. 2a, this causes the blood flow to favor the side of the oxygenator on which the outlet 28 is located. In accordance with one aspect of the invention, the packing density (i.e. the pressure exerted by the packing roller 22) is increased somewhat on the side of the fiber bundle 24 on which the outlet 28 is located, as opposed to the packing density on the side away from outlet 28. This causes the blood to flow somewhat less freely on the outlet side than on the opposite side, and results in a pattern that better utilizes the available fiber (FIG. 2b).

The circumferentially varying packing described above is preferably created, according to the invention, by synchronizing the rotation of the packing roller 22 with that of the core, and increasing the packing pressure whenever the core rotates through a predetermined portion of its rotational arc. This can be done by making the packing roller 22 of the same diameter as the core 20 and slightly eccentric (FIG. 3)

or by using a servomechanism 30 (FIG. 4a) to cyclically vary the pressure (FIG. 4b) as a function of the angular position of core 20.

Figure 5:
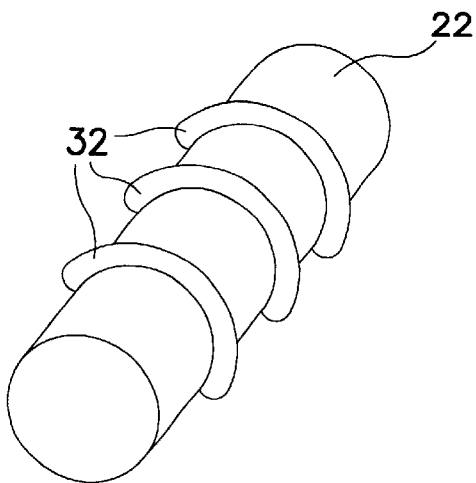
FIG. 5 is a perspective view of a packing roller used in a third embodiment of the invention.
Figure 6:
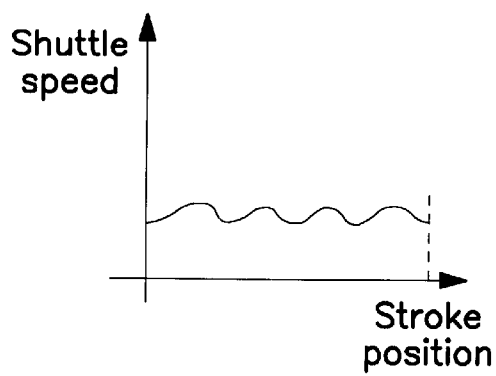
FIG. 6 is a stroke position—shuttle speed diagram illustrating a fourth embodiment of the invention.

In accordance with another aspect of the invention, mixing of the blood flow is improved by varying the packing density in a longitudinal direction along the fiber bundle 24 to break up laminar flow channels. This is preferably accomplished either by providing the packing roller 22 with annular protrusions 32 (FIG. 5), or by varying the speed of the shuttle 18 as it travels along the core 20 (FIG. 6). The latter varies packing density by varying the number of fibers per centimeter wound onto the core 20 at any given stroke position of the shuttle 18.

It should be understood that the exemplary variable packing density methods described herein and shown in the drawings represent only presently preferred embodiments of the invention. Indeed, various modifications and additions may be made to such embodiments without departing from the spirit and scope of the invention. Thus, other modifications and additions may occur to those skilled in the art and may be implemented to adapt the present invention for use in a variety of different applications.

We claim:

1. A blood oxygenator, comprising:
   a) a substantially cylindrical core having a central axis defining a longitudinal direction;
   b) a substantially cylindrical housing having a curved, cylindrical wall with a blood outlet at a first, longitudinally extending side portion thereof and a second longitudinally extending side portion having no blood outlet; and
   c) a substantially cylindrical bundle of packed criss-cross wound layers of hollow fibers disposed between said core and housing substantially coaxially therewith and having an outer side adjacent the curved, cylindrical wall of the housing;
   d) the packing density of said hollow fibers varying in the fiber bundle such that the packing density is greater on a portion of the fiber bundle adjacent the first longitudinally extending side portion of the curved, cylindrical wall than on a portion of the fiber bundle adjacent the second longitudinally extending portion of the curved, cylindrical side wall such that the blood flows less freely through the portion of the fiber bundle adjacent the first side portion of the curved, cylindrical wall than through the portion of the fiber bundle adjacent the second longitudinally extending side portion of the curved, cylindrical wall.

2. The oxygenator of claim 1 in which said packing density is varied by variation of compression of said layers against each other.

3. A blood oxygenator, comprising:
   a) an elongated, substantially cylindrical core having a central axis defining a longitudinal direction;
   b) a substantially cylindrical housing; and
   c) a substantially cylindrical bundle of packed criss-cross wound layers of hollow fibers disposed between said core and housing, the bundle formed substantially coaxially around and extending in the longitudinal direction along the core, the packing density of said hollow fibers varying in the fiber bundle along the longitudinal direction by variation of compression of said layers against each other such that the packing density is greater in a first longitudinal portion of the fiber bundle than in a second longitudinal portion of the fiber bundle.

4. A blood oxygenator, comprising:
   a) an elongated, substantially cylindrical core having a central axis defining a longitudinal direction;
   b) a substantially cylindrical housing; and
   c) a substantially cylindrical bundle of packed criss-cross wound layers of hollow fibers disposed between said core and housing, the bundle formed substantially coaxially around and extending in the longitudinal direction along the core, the packing density of said hollow fibers varying in the fiber bundle by variation of compression of said layers against each other along a circumference around the longitudinal direction such that the packing density is greater in a first circumferential portion of the fiber bundle than in a second circumferential portion of the fiber bundle.

\* \* \* \* \*